US007585966B1

(12) United States Patent
Kealey et al.

(10) Patent No.: US 7,585,966 B1
(45) Date of Patent: Sep. 8, 2009

(54) INHIBITORY POLYNUCLEOTIDES DIRECTED AGAINST THE RNA COMPONENT OF TELOMERASE

(75) Inventors: James T. Kealey, San Anselmo, CA (US); Ronald Pruzan, Palo Alto, CA (US); Scott L. Weinrich, Redwood City, CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 09/436,060

(22) Filed: Nov. 8, 1999

Related U.S. Application Data

(63) Continuation of application No. 08/770,564, filed on Dec. 20, 1996, now abandoned.

(51) Int. Cl.
C07H 21/02 (2006.01)
C07H 21/04 (2006.01)

(52) U.S. Cl. .................... 536/24.5; 536/23.1; 536/24.3; 536/24.33

(58) Field of Classification Search .................. 435/6, 435/91.1, 91.31, 440, 320.1, 325, 366, 375; 514/44; 536/23.1, 23.2, 24.81, 24.5
See application file for complete search history.

(56) References Cited

U.S. PATENT DOCUMENTS 5,583,016 A * 12/1996 Villeponteau et al.

5,770,422 A * 6/1998 Collins ........................ 435/194
5,776,679 A * 7/1998 Villeponteau et al. .......... 435/6
5,846,723 A * 12/1998 Kim et al. ....................... 435/6
5,968,506 A * 10/1999 Weinrich et al. ........... 424/94.5
6,261,556 B1 7/2001 Weinrich et al.

FOREIGN PATENT DOCUMENTS

| WO | WO 95/13381 | | 5/1995 |
| WO | WO 96/01614 | * | 1/1996 |
| WO | WO 96/01835 | | 1/1996 |
| WO | WO 96/40868 | * | 12/1996 |

OTHER PUBLICATIONS

Branch, A.D. TIBS vol. 23, Feb. 1998, pp. 45-50.*
Jen et al., Stem Cells 2000; 18:307-319.*
Green et al., J.A. Coll. Surg., (Jul. 2000).*
Anderson, W.F., Human Gene Therapy, Nature, vol. 392, SUPP. 30, (Apr. 1998), Feb. 1998.*
Skerra, A. Phosphorothioate primers improve the amplification of DNA sequences by DNA polymerases with proofreading activity. Nucleic Acids Research, 1992 vol. 20:3551-3554.*
Nakamaye et al. Direct sequencing of polymerase chain reaction amplified DNA fragments through the incorporation of deoxynucleoside alpha-thiotriphosphates. Nucleic Acids Research, 1988 vol. 16:9947-9959.*

(Continued)

*Primary Examiner*—Sean McGarry
*Assistant Examiner*—Terra Cotta Gibbs
(74) *Attorney, Agent, or Firm*—Leslie A. Mooi; David J. Earp

(57) ABSTRACT

This invention provides inhibitory polynucleotides, such as antisense molecules, directed against accessible regions in the telomerase ribonucleoprotein. The polynucleotides are useful for inhibiting the activity of telomerase in cells and for treating cancer.

9 Claims, 1 Drawing Sheet

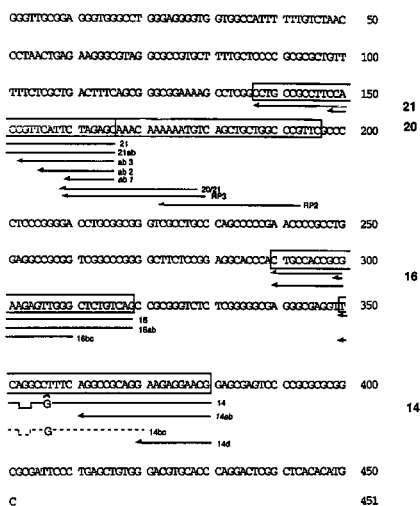

OTHER PUBLICATIONS

Branch, TIBS 23, 45-50 (Feb. 1998).*

Rojanasakul, Antisense Oligonucleotide Therapeutics: Drug Delivery and Targeting, Advanced Drug Delivery Reviews 18, 115-131 (1996), 1995.*

Hodgson, Advances in Vector Systems for Gene Therapy, 5(5) Exp. Opin. Ther. Patents 459-468 (May 1995).*

Gewirtz et al, Facilitating Oligonucleotide Delivery: Helping Antisense Deliver On Its Promise, 93 PNAS 3161 (Apr. 1996).*

Albanell et al., "Telomerase Activity Is Repressed During Differentiation of Maturation-Sensitive but Not Resistant Human Tumor Cell Lines," *Cancer Research*, 56:1503-1508 (1996).

Avilion et al., "Human Telomerase RNA and Telomerase Activity in Immortal Cell Lines and Tumor Tissues," *Cancer Research*, 56:645-650 (1996).

Blasco et al., "Functional Characterization and Developmental Regulation of Mouse Telomerase RNA," *Science*, 269:1267-1270 (1995).

Bodnar et al., "Mechanism of Telomerase Induction During T Cell Activation," *Experimental Cell Research*, 228:58-68, Article No. 0299 (1996).

Branch, *TIBS*, 23:45-50 (Feb. 1998).

Feng et al., "The RNA Component of Human Telomerase," *Science*, 269:1236-1241 (1995).

Gewirtz et al., "Facilitating Oligonucleotide Delivery: Helping Antisense Deliver on Its Promise," *PNAS*, 93:3161 (Apr. 1996).

Harley et al., "Telomeres and Telomerase in Aging and Cancer," *Current Opinion in Genetics and Development*, 5:249-255 (1995).

Hodgson, "Advances in Vector Systems for Gene Therapy," *Opin. Ther. Patents*, 5(5):459-468 (1995).

Kim et al., "Specific Association of Human Telomerase Activity with Immortal Cells and Cancer," *Science*, 266:2011-2015 (1994).

Rojanasakul et al., "Antisense Oligonucleotide Therapeutics: Drug Delivery and Targeting," *Advanced Drug Delivery Reviews*, 18:115-131 (1996).

Villeponteau, "The RNA Components of Human and Mouse Telomerases," *Seminars in Cell and Development Biology*, 7:15-21 (1996).

Khan et al., "Polymerase chain reaction assay of mRNA using 28S rRNA as internal standard" *Neuroscience Letters* 147:114-117 (1992).

* cited by examiner

Figure 1: Accessibility of hTR in native human telomerase. All antisense ligands direct RNase H cleavage of hTR, except 14bc (dotted). Although RP2 and RP3 were not directly tested via RNase H assay (they are 2'OMe RNA antisense ligands), DNA oligo 20/21 (similar to RP3) directed RNase H cleavage of hTR, and a 30mer DNA oligo directed to region "20" (containing the RP2 sequence) yielded marginal RNase H cleavage of hTR.

```
GGGTTGCGGA GGGTGGGCCT GGGAGGGGTG GTGGCCATTT TTTGTCTAAC    50

CCTAACTGAG AAGGGCGTAG GCGCCGTGCT TTTGCTCCCC GCGCGCTGTT   100

TTTCTCGCTG ACTTTCAGCG GGCGGAAAAG CCTCGGCCTG CCGCCTTCCA   150      21

CCGTTCATTC TAGAGCAAAC AAAAAATGTC AGCTGCTGGC CCGTTCGCCC   200      20
             21
             21ab
             ab3
             ab2
             ab1
                   20/21
                   RP3
                              RP2

CTCCCGGGGA CCTGCGGCGG GTCGCCTGCC CAGCCCCCGA ACCCCGCCTG   250

GAGGCCGCGG TCGGCCCGGG GCTTCTCCGG AGGCACCCAC TGCCACCGCG   300      16

AAGAGTTGGG CTCTGTCAGC CGCGGGTCTC TCGGGGCCGA GGGCGAGGTT   350
          16
          16ab
          16bc

CAGGCCTTTC AGGCCGCAGG AAGAGGAACG GAGCGAGTCC CCGCGCGCGG   400
         G                         14                            14
                                   14ab
         G                         14bc
                                   14d

CGCGATTCCC TGAGCTGTGG GACGTGCACC CAGGACTCGG CTCACACATG   450

C                                                         451
```

INHIBITORY POLYNUCLEOTIDES DIRECTED AGAINST THE RNA COMPONENT OF TELOMERASE

CROSS REFERENCE TO RELATED APPLICATION

This application is a Continuation of U.S. application Ser. No. 08/770,564, filed Dec. 20, 1996 now abandoned.

BACKGROUND OF THE INVENTION

The present invention relates to methods and compositions for inhibiting the activity of telomerase enzyme.

Nearly all bodily cells possess finite capacity to divide and replicate. One mechanism that regulates this finite life span involves telomeres, which are specialized structures found at the end of chromosomes and composed of protein and DNA having the repeated sequence, TTAGGG. Telomeres shorten each time a cell divides until they critically short. This event is associated with the onset of cell senescence, after which the senescent cell ceases to proliferate.

In contrast, certain cells are "immortal" and have the capacity to divide indefinitely. Such cells include, for example, single-celled eukaryotic organisms, germline cells (i.e., oocytes and sperm), certain human cell cultures and cancer cells. These cells do not exhibit telomere shortening upon cell division. Most of these cells, including about 90% of primary cancers, exhibit the activity of an enzyme, telomerase. Mortal bodily cells exhibit very little or no telomerase activity. The amount of hTR in cancer cell lines is two- to seven-fold higher than the amount in normal cells (Feng et al., supra).

Telomerase is a ribonucleoprotein that regulates the length of telomeres. Telomerase acts as a DNA polymerase, adding telomeric repeat sequences to the chromosomes' ends using a sequence within the RNA component of telomerase as a template. The RNA component of human telomerase, hTR, has been isolated. Feng et al. (1995) *Science* 269:1236-41 and U.S. Pat. No. 5,583,016.

Inhibiting telomerase activity in immortal cells, such as cancer cells, leads to telomere shortening and cell death. Feng et al., supra, showed that transfecting an immortalized cell line, HeLa, with expression vectors that expressed hTR antisense transcripts resulted in telomere shortening and cell crisis characterized by a marked inhibition of cell growth. Thus, inhibition of telomerase activity in cancer cells is a target for therapeutic intervention.

SUMMARY OF THE INVENTION

Inhibitory polynucleotides directed against the RNA component of mammalian telomerases (especially the RNA component of human telomerase ("hTR")) are useful for inhibiting telomerase activity either in samples containing telomerase or in cells, including cultured cells or cells in vivo. Inhibitory polynucleotides include, for example, antisense, sense, ribozyme and triple helix-forming polynucleotides. The inhibitory polynucleotides of the invention have a sequence of at least 7 nucleotides that specifically hybridize to a nucleotide sequence within the RNA component of telomerase, the primary RNA transcript or a genomic sequence (either DNA strand) of the telomerase RNA component gene or around it (e.g., the telomerase promoter).

Inhibitory polynucleotides directed against sequences of the RNA component of telomerase can inhibit the telomerase activity level in a cell by interfering with transcription of the RNA component, decreasing the half-life of the telomerase RNA component transcript, inhibiting assembly of the RNA component into the telomerase holoenzyme, or inhibiting the polymerase activity of telomerase.

Regions of the RNA component of human telomerase in the telomerase holoenzyme have been discovered that are accessible to hybridization with antisense polynucleotides. Interestingly, several of these regions are outside the template area of hTR, nucleotides 46-55. These regions are attractive areas to direct inhibitory polynucleotides for inhibiting telomerase activity.

In one aspect, this invention provides a polynucleotide comprising an antisense sequence of at least 7 nucleotides that specifically hybridizes to a nucleotide sequence within an accessible region of the RNA component of a mammalian telomerase, in particular, the RNA component of human telomerase. In one embodiment, the polynucleotide does not specifically hybridize to a nucleotide sequence within the template region of the RNA component of telomerase. In one embodiment of the polynucleotide, the antisense sequence is at most 50 nucleotides. The sequence of the polynucleotide can consist essentially or exclusively of the antisense sequence. The antisense sequence can be complementary to the nucleotide sequence within an accessible region. In one embodiment, the accessible region is a sequence selected from nucleotides 137-196, 290-319, and 350-380 of hTR (SEQ ID NO:1). In certain embodiments, the polynucleotide comprises DNA, RNA, or a nucleotide analog selected from phosphorothioates, phosphoramidates, methyl phosphonates, chiral-methyl phosphonates, 2-O-methyl ribonucleotides, peptide-nucleic acids (PNAs), and the like. In another embodiment, the polynucleotide of further comprises an inhibitory moiety.

In another aspect, this invention provides an expression vector comprising a recombinant polynucleotide comprising expression control sequences operatively linked to a nucleotide sequence encoding polynucleotide comprising an antisense sequence of at least 7 nucleotides that specifically hybridizes to a nucleotide sequence within an accessible region of the RNA component of telomerase, but that does not hybridize to a sequence within the template region of the telomerase. The expression vector can be a viral vector or a plasmid vector comprising the recombinant polynucleotide.

In another aspect, this invention provides a method of inhibiting mammalian telomerase activity in a mammalian cell comprising the step of providing the cell with a polynucleotide comprising an antisense sequence of at least 7 nucleotides that specifically hybridizes to a nucleotide sequence within an accessible region of the RNA component of the telomerase but that does not hybridize to a sequence within the template region of the telomerase. In one embodiment the step of providing the polynucleotide comprises transfecting the cell with an expression vector comprising expression control sequences operatively linked to a nucleotide sequence encoding the polynucleotide which vector expresses the antisense polynucleotide. The polynucleotide inhibits the activity of the telomerase in cells expressing that enzyme. The cell can be a cancer cell, a germ-line cell, a hematopoietic cell or a telomerase-expressing cell in culture.

In another aspect, this invention provides a pharmaceutical composition comprising a pharmaceutically acceptable carrier and (1) a polynucleotide comprising an antisense sequence of at least 7 nucleotides that specifically hybridizes to a nucleotide sequence within an accessible region of the RNA component of telomerase but that does not hybridize to a sequence within the template region of the telomerase, or (2) an expression vector comprising expression control sequences operatively linked to a nucleotide sequence encoding the polynucleotide, which vector expresses the polynucleotide.

In another aspect, this invention provides a method of treating a telomerase-related condition involving cells exhibiting telomerase activity in a subject. The method comprises the step of administering to the subject a pharmaceutical composition in an amount effective to inhibit telomerase activity in the cells, wherein the pharmaceutical composition comprises a pharmaceutically acceptable carrier and (1) a polynucleotide comprising an antisense sequence of at least 7 nucleotides that specifically hybridizes to a nucleotide sequence within an accessible region of the RNA component of the mammalian telomerase but that does not hybridize to a sequence within the template region of the telomerase, or (2) an expression vector comprising expression control sequences operatively linked to a nucleotide sequence encoding the polynucleotide which vector expresses the polynucleotide. Inhibiting telomerase activity in the cells provides the treatment of the condition. In one embodiment, the telomerase-related condition is cancer and inhibition of telomerase activity in the cancer cells inhibits the growth of the cancer. In another embodiment the pharmaceutical composition is an injectable solution administered by injection.

In another aspect, this invention provides a ribozyme that cleaves the RNA component of a mammalian telomerase and, in particular, cleaves a nucleotide sequence within an accessible region of the RNA component of a mammalian telomerase. This invention also provides expression vectors comprising a recombinant polynucleotide comprising expression control sequences encoding the ribozyme. In another aspect, this invention provides methods of inhibiting telomerase activity in a cell by providing the cell with the ribozyme or with an expression vector comprising expression control sequences operatively linked to nucleotide sequences encoding the ribozyme. In one embodiment, the invention provides pharmaceutical compositions comprising the ribozyme or the expression vector. In another aspect, the invention provides a method of treating a telomerase-related condition, such as cancer or fertility, by administering to the subject the pharmaceutical composition.

BRIEF DESCRIPTION OF THE DRAWING

FIG. 1 presents the nucleotide sequence of the RNA component of human telomerase (SEQ ID NO:29) (nucleotides 266-716 of SEQ ID NO:1). The boxed areas, from nucleotides 137-196, 290-319 and 350-380, indicate regions of hTR accessible in the telomerase holoenzyme. Antisense molecules, indicated by numbers below the hTR sequence, have sequences complementary to the hTR sequence indicated by the arrows.

DETAILED DESCRIPTION OF THE INVENTION

I. Definitions

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2d ed. 1994); *The Cambridge Dictionary of Science and Technology* (Walker ed., 1988); and Hale & Marham, *The Harper Collins Dictionary of Biology* (1991). Although any methods and materials similar or equivalent to those described herein can be used in the practice or testing of the present invention, preferred methods and materials are described. As used herein, the following terms have the meanings ascribed to them unless specified otherwise.

"Polynucleotide" refers to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of polypeptide sequences is the amino-terminus; the right-hand end of polypeptide sequences is the carboxyl-terminus.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

A "reference sequence" is a defined sequence used as a basis for a sequence comparison and may be a subset of a larger sequence, e.g., a complete cDNA, protein, or gene sequence.

Because two polynucleotides or polypeptides each may comprise (1) a sequence (i.e., only a portion of the complete polynucleotide or polypeptide sequence) that is similar between the two polynucleotides, or (2) a sequence that is divergent between the two polynucleotides, sequence comparisons between two (or more) polynucleotides or polypeptides are typically performed by comparing sequences of the two polynucleotides over a "comparison window" to identify and compare local regions of sequence similarity.

A "comparison window" refers to a conceptual segment of typically at least 12 consecutive nucleotide or 4 consecutive amino acid residues that is compared to a reference sequence. The comparison window frequently is at least 15 or at least 25 nucleotides in length or at least 5 or at least 8 amino acids in length. The comparison window may comprise additions or deletions (i.e., gaps) of about 20 percent or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Dr., Madison, Wis.) or by inspection, and the best alignment (i.e., resulting in the highest percentage of homology over the comparison window) generated by any of the various methods is selected.

A subject nucleotide sequence or amino acid sequence is "identical" to a reference sequence if the two sequences are the same when aligned for maximum correspondence over the length of the nucleotide or amino acid sequence.

The "percentage of sequence identity" between two sequences is calculated by comparing two optimally aligned sequences over a comparison window, determining the number of positions at which the identical nucleotide or amino acid occurs in both sequences to yield the number of matched positions, dividing the number of matched positions by the total number of positions in the window of comparison (i.e., the window size), and multiplying the result by 100 to yield the percentage of sequence identity.

When percentage of sequence identity is used in reference to polypeptides it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to known algorithm. See, e.g., Meyers & Miller, *Computer Applic. Biol. Sci.,* 4: 11-17 (1988); Smith & Waterman, *Adv. Appl. Math.* 2: 482 (1981); Needleman & Wunsch, *J. Mol. Biol.* 48: 443 (1970); Pearson & Lipman, *Proc. Natl. Acad. Sci. USA* 85: 2444 (1988); Higgins & Sharp *Gene,* 73: 237-244 (1988); Higgins & Sharp, *CABIOS* 5: 151-153 (1989); Corpet et al., *Nucleic Acids Research* 16: 10881-90 (1988); Huang et al., *Computer Applications in the Biosciences* 8: 155-65 (1992); and Pearson et al., *Methods in Molecular Biology* 24: 307-31 (1994). Alignment is also often performed by inspection and manual alignment.

A subject nucleotide sequence or amino acid sequence is "substantially identical" to a reference sequence if the subject amino acid sequence or nucleotide sequence has at least 80% sequence identity over a comparison window. Thus, sequences that have at least 85% sequence identity, at least 90% sequence identity, at least 95% sequence identity or at least 99% sequence identity with the reference sequence are also substantially identical. Two sequences that are identical to each other are, of course, also substantially identical.

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotides of the first polynucleotide have the sequence of the nucleotides in the polynucleotide binding partner of the second polynucleotide. Thus, the polynucleotide whose sequence 5'-TATAC-3' is complementary to a polynucleotide whose sequence is 5'-GTATA-3'.

A nucleotide sequence is "substantially complementary" to a reference nucleotide sequence if the sequence complementary to the subject nucleotide sequence is substantially identical to the reference nucleotide sequence.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA, mRNA and other RNA molecules such as hTR) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Recombinant" refers to polynucleotides synthesized or otherwise manipulated in vitro ("recombinant polynucleotides") and to methods of using recombinant polynucleotides to produce gene products encoded by those polynucleotides in cells or other biological systems. For example, an amplified or assembled product polynucleotide may be inserted into a suitable DNA vector, such as a bacterial plasmid, and the plasmid can be used to transform a suitable host cell. A host cell that comprises the recombinant polynucleotide is referred to as a "recombinant host cell". The gene is then expressed in the recombinant host cell to produce, e.g., a "recombinant protein." A recombinant polynucleotide may serve a non-coding function (e.g., promoter, origin of replication, ribosome-binding site, etc.) as well.

"Pharmaceutical composition" refers to a composition suitable for pharmaceutical use in a mammal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in *Remington's Pharmaceutical Sciences,* 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, or intravenous intraperitoneal injection; or topical, transdermal, or transmucosal administration).

"Specifically binds to" refers to the ability of one molecule, typically a molecule such as an antibody or polynucleotide, to contact and associate with another specific molecule even in the presence of many other diverse molecules. For example, a single-stranded polynucleotide can "specifically bind to" a single-stranded polynucleotide that is complementary in sequence, and an antibody "specifically binds to" or "is specifically immunoreactive with" its corresponding antigen. Thus, under designated immunoassay conditions, an antibody binds preferentially to a particular protein and not in a significant amount to other proteins present in the sample. Specific binding to a protein under such conditions requires an antibody selected for its specificity for a particular protein. To select antibodies specifically immunoreactive with a particular protein, one can employ a variety of means, i.e., solid-phase ELISA immunoassays are routinely used to select monoclonal antibodies specifically immunoreactive with a protein. See Harlow & Lane, *Antibodies, A Laboratory Manual,* Cold Spring Harbor Publications, New York (1988).

A polynucleotide "specifically hybridizes" to a target polynucleotide if the polynucleotide hybridizes to the target under stringent conditions. "Stringent conditions" refers to temperature and ionic conditions used in nucleic acid hybridization. Stringent conditions depend upon the various components present during hybridization. Generally, stringent conditions are selected to be about 10° C., and preferably about 5° C. lower than the thermal melting point ($T_m$) for the specific sequence at a defined ionic strength and pH. The $T_m$ is the temperature (under defined ionic strength and pH) at which 50% of a target sequence hybridizes to a complementary polynucleotide.

A first sequence is an "antisense sequence" with respect to a second sequence if a polynucleotide whose sequence is the first sequence specifically hybridizes with a polynucleotide whose sequence is the second sequence.

"Substantially pure" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80 to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition.

"Suitable reaction conditions" are those conditions suitable for conducting a specified reaction using commercially available reagents. Such conditions are known or readily established by those of skill in the art for a variety of reactions. For example, suitable polymerase chain reaction (PCR) conditions include those conditions specified in U.S. Pat. Nos. 4,683,202; 4,683,195; 4,800,159; and 4,965,188. As one example and not to limit the invention, suitable reaction conditions can comprise: 0.2 mM each dNTP, 2.2 mM $MgCl_2$, 50 mM KCl, 10 mM Tris-HCl, pH 9.0, and 0.1% Triton X-100.

"Telomerase" or "telomerase ribonucleoprotein complex" refers to a ribonucleoprotein enzyme of eukaryotic origin identifiable by its ability to polymerize a DNA sequence of a eukaryotic telomere. Telomerase is further characterized by an RNA component having sequences complementary to at least part of the telomeric repeat of the source species and by one or more protein components. As used herein, "mammalian telomerase" and "human telomerase" refer to telomerases that can be found naturally in various mammalian or human cells, respectively, or having polypeptide components with the same amino acid sequences, and RNA components with the same nucleotide sequences. Human telomerase contains the RNA component, "hTR." The term "telomerase" includes all allelic forms of telomerase, including wild-type and mutant forms.

"Telomerase activity" refers to the synthesis of telomeric DNA by telomerase. A preferred assay method for detecting telomerase activity is the TRAP assay. See International Application published under the PCT, WO 95/13381. This assay measures the amount of radioactive nucleotides incorporated into elongation products, polynucleotides, formed by nucleotide addition to a telomerase substrate or primer. The radioactivity incorporated can be measured as a function of the intensity of a band on a PhosphorImager™ screen exposed to a gel on which the radioactive products are separated. A test experiment and a control experiment can be compared by visually using the PhosphorImager™ screens. See also the commercially available TRAP-eze telomerase assay kit (Oncor); and Morin, *Cell* 59: 521-529 (1989).

"Telomerase-related condition" refers to a condition in a subject maintained by telomerase activity within cells of the individual. Telomerase-related conditions include, e.g., cancer (telomerase-activity in malignant cells), fertility (telomerase activity in germ-line cells) and hematopoiesis (telomerase activity in hematopoietic stem cells).

"Accessible region of the RNA component of telomerase" refers to a region of an RNA component of telomerase (e.g., hTR) to which an antisense polynucleotide can specifically hybridize when the RNA component is part of the telomerase ribonucleoprotein complex.

The "template region" of the RNA component of mammalian telomerase refers to a subsequence of the RNA component of mammalian telomerase that serves as a template for synthesis of telomeric repeats. All vertebrates appear to have the conserved sequence 5'-TTAGGG-3' at chromosome ends, although subtelomeric sequences can vary (See, e.g., Harley & Villeponteau, *Current Opin. in Gen. and Dev.* 5: 249-255 (1995)). The template region is complementary to at least the single telomeric repeat sequence, and can also include a second portion of the telomeric repeat sequence. For example, the template region of hTR is 5'-CTAACCCTAA-3', nucleotides 46-55 of hTR (nucleotides 311-320 of SEQ ID NO:1).

II. The RNA Component of Mammalian Telomerase

A. Mammalian Telomerase

Mammalian telomerase includes an RNA component. The RNA component of telomerase from humans and from mice have been isolated and sequenced. See, e.g., Feng et al. (1995) *Science* 269:1236-41, U.S. Pat. No. 5,583,016 and Blasco et al. (1995) *Science* 269:1267-1270.

B. The Sequence of hTR

Human genomic DNA encoding hTR has been cloned, sequenced and placed on deposit. A lambda clone designated "28-1" contains an ~15 kb insert containing human telomerase RNA component gene sequences. Clone 28-1 was deposited with the American Type Culture Collection pursuant to the Budapest Treaty and granted accession number ATCC 75925. Plasmid pGRN33 contains an ~2.5 kb HindIII-SacI insert containing sequences from lambda clone 28-1 that contain the sequence of hTR. Plasmid pGRN33 was deposited with the American Type Culture Collection pursuant to the Budapest Treaty and granted accession number ATCC 75926. A PstI fragment of the ~2.4 kb SauIIIA-HindIII fragment of clone 28-1 also contains the hTR sequence. The sequence of the PstI fragment is provided in SEQ ID NO:1, below. The nucleotides of hTR are indicated above the sequence indicated by stars and numbered 1 to 451. The sequence of hTR contained within SEQ ID NO:1 is separately set forth in SEQ ID NO:16. The template region is underlined.

```
  1 CTGCAGAGGATAGAAAAAAGGCCCTCTGATACCTCAAGTTAGTTTCACCTTTAAAGAAGG
    GACGTCTCCTATCTTTTTTCCGGGAGACTATGGAGTTCAATCAAAGTGGAAATTTCTTCC
    -PST1-

61 TCGGAAGTAAAGACGCAAAGCCTTTCCCGGACGTGCGGAAGGGCAACGTCCTTCCTCATG
    AGCCTTCATTTCTGCGTTTCGGAAAGGGCCTGCACGCCTTCCCGTTGCAGGAAGGAGTAC

121 GCCGGAAATGGAACTTTAATTTCCCGTTCCCCCCAACCAGCCCGCCCGAGAGAGTGACTC
    CGGCCTTTACCTTGAAATTAAAGGGCAAGGGGGGTTGGTCGGGCGGGCTCTCTCACTGAG

181 TCACGAGAGCCGCGAGAGTCAGCTTGGCCAATCCGTGCGGTCGGCGGCCGCTCCCTTTAT
    AGTGCTCTCGGCGCTCTCAGTCGAACCGGTTAGGCACGCCAGCCGCCGGCGAGGGAAATA 1           10          20          30
                                ************************************
241 AAGCCGACTCGCCCGGCAGCGCACCGGGTTGCGGAGGGTGGGCCTGGGAGGGGTGGTGGC
    TTCGGCTGAGCGGGCCGTCGCGTGGCCCAACGCCTCCCACCCGGACCCTCCCCACCACCG 40          50          60          70          80          90
                ************************************************************
301 CATTTTTTGTCTAACCCTAACTGAGAAGGGCGTAGGCGCCGTGCTTTTGCTCCCCGCGCG
    GTAAAAAACAGATTGGGATTGACTCTTCCCGCATCCGCGGCACGAAAACGAGGGGCGCGC 100         110         120         130         140         150
                ************************************************************
361 CTGTTTTTCTCGCTGACTTTCAGCGGGCGGAAAAGCCTCGGCCTGCCGCCTTCCACCGTT
    GACAAAAAGAGCGACTGAAAGTCGCCCGCCTTTTCGGAGCCGGACGGCGGAAGGTGGCAA 160         170         180         190         200         210
                ************************************************************
421 CATTCTAGAGCAAACAAAAAATGTCAGCTGCTGGCCCGTTCGCCCCTCCCGGGGACCTGC
    GTAAGATCTCGTTTGTTTTTACAGTCGACGACCGGGCAAGCGGGGAGGGCCCCTGGACG

HTR
                220         230         240         250         260         270
                ************************************************************
481 GGCGGGTCGCCTGCCCAGCCCCCGAACCCCGCCTGGAGGCCGCGGTCGGCCCGGGGCTTC
    CCGCCCAGCGGACGGGTCGGGGGCTTGGGCGGACCTCCGGCGCCAGCCGGGCCCCGAAG 280         290         300         310         320         330
                ************************************************************
541 TCCGGAGGCACCCACTGCCACCGCGAAGAGTTGGGCTCTGTCAGCCGCGGGTCTCTCGGG
    AGGCCTCCGTGGGTGACGGTGGCGCTTCTCAACCCGAGACAGTCGGCGCCCAGAGAGCCC 340         350         360         370         380         390
                ************************************************************
601 GGCGAGGGCGAGGTTCAGGCCTTTCAGGCCGCAGGAAGAGGAACGGAGCGAGTCCCCGCG
    CCGCTCCCGCTCCAAGTCCGGAAAGTCCGGCGTCCTTCTCCTTGCCTCGCTCAGGGCGC 400         410         420         430         440         450
                ******************************************************
661 CGCGGCGCGATTCCCTGAGCTGTGGGACGTGCACCCAGGACTCGGCTCACACATGCAGTT
    GCGCCGCGCTAAGGGACTCGACACCCTGCACGTGGGTCCTGAGCCGAGTGTGTACGTCAA
```

```
721 CGCTTTCCTGTTGGTGGGGGGAACGCCGATCGTGCGCATCCGTCACCCCTCGCCGGCAGT
    GCGAAAGGACAACCACCCCCCTTGCGGCTAGCACGCGTAGGCAGTGGGGAGCGGCCGTCA

781 GGGGGCTTGTGAACCCCCAAACCTGACTGACTGGGCCAGTGTGCTGCAAATTGGCAGGAG
    CCCCCGAACACTTGGGGGTTTGGACTGACTGACCCGGTCACACGACGTTTAACCGTCCTC

841 ACGTGAAGGCACCTCCAAAGTCGGCCAAAATGAATGGGCAGTGAGCCGGGGTTGCCTGGA
    TGCACTTCCGTGGAGGTTTCAGCCGGTTTTACTTACCCGTCACTCGGCCCCAACGGACCT

901 GCCGTTCCTGCGTGGGTTCTCCCGTCTTCCGCTTTTTGTTGCCTTTTATGGTTGTATTAC
    CGGCAAGGACGCACCCAAGAGGGCAGAAGGCGAAAAACAACGGAAAATACCAACATAATG

961 AACTTAGTTCCTGCTCTGCAG (SEQ ID NO:1)
    TTGAATCAAGGACGAGACGTC
                -PST1-
```

C. Regions of hTR Accessible in the Telomerase Ribonucleoprotein

Regions of hTR that are accessible in the native telomerase ribonucleoprotein have been identified. The regions were identified in two ways. The first way involved contacting samples containing human telomerase with a variety of DNA polynucleotides having sequences complementary to the sequence of hTR under hybridization conditions, contacting the telomerase with RNase H, which digests the RNA strand of an RNA-DNA hybrid, and determining whether hTR had been cleaved. Antisense oligonucleotides that supported hTR cleavage were complementary to nucleotides 137-166, 290-319 and 350-380 of hTR. See Table 1 and FIG. 1. Specific polynucleotides capable of supporting RNase H cleavage are described in more detail in the Example. The second way involved oligo-decoration. This method indicated that nucleotides 167-196 also are accessible. Regions of hTR accessible in the telomerase ribonucleoprotein comprise these areas. Other accessible areas of hTR can be identified by similar assays using antisense polynucleotides whose sequences are substantially complementary to a nucleotide sequence selected from hTR. The RNA component of telomerase of other mammals also contains accessible regions in the telomerase ribonucleoprotein.

Accessible regions of the RNA component of telomerase and their uses are also described in U.S. Pat. No. 5,846,723, filed Dec. 20, 1996.

III. Inhibitory Polynucleotides

A. General

This invention provides inhibitory polynucleotides directed against the RNA component of telomerase that inhibit telomerase activity. Inhibitory polynucleotides can inhibit telomerase activity in a number of ways. According to one mechanism, the polynucleotide prevents transcription of the telomerase RNA component gene (for instance, by triple helix formation). In another mechanism, the polynucleotide destabilizes the telomerase RNA component and reduces its half-life. In another mechanism, the polynucleotide inhibits assembly of the RNA component into the telomerase ribonucleoprotein by binding to the RNA component of telomerase. In another mechanism, the polynucleotide inhibits the polymerase activity of the telomerase ribonucleoprotein, e.g., by binding to an accessible region in telomerase or by inhibiting the polymerase activity of telomerase.

An inhibitory polynucleotide is a polynucleotide that is capable of hybridizing under stringent conditions with a target polynucleotide and that interferes with the transcription, processing, translation or other of the target polynucleotide. Inhibitory polynucleotides generally are single-stranded and have a sequence of at least 7, 8, 9, 10, or 11 nucleotides capable of specifically hybridizing to the target sequence. RNA sequences generally require a sequence of at least 10 nucleotides for specific hybridization. Inhibitory polynucleotides include, without limitation, antisense molecules, ribozymes, sense molecules and triplex-forming molecules.

While not wishing to be limited by theory, it is believed that inhibitory polynucleotides inhibit the function of a target, in part, by binding to the appropriate target sequence. An inhibitory polynucleotide can inhibit DNA replication or DNA transcription by, for example, interfering with the attachment of DNA or RNA polymerase to the promoter by binding to a transcriptional initiation site or a template. It can interfere with processing of mRNA, poly(A) addition to mRNA or translation of mRNA by, for example, binding to regions of the RNA transcript such as the ribosome binding site. It can promote inhibitory mechanisms of the cells, such as promoting RNA degradation via RNase action. The inhibitory polynucleotide can bind to the major groove of the duplex DNA to form a triple helical or "triplex" structure. Methods of inhibition using inhibitory polynucleotides therefore encompass a number of different approaches to altering expression of specific genes that operate by different mechanisms. These different types of inhibitory polynucleotide technology are described in C. Helene and J. Toulme, (1990) *Biochim. Biophys. Acta.*, 1049:99-125.

The literature also provides examples of antisense polynucleotide inhibition of the function of ribonucleoproteins. Hence, for ribonucleoprotein complexes that contain a functional RNA (e.g., snRNAP complexes involved in RNA splicing), it has been shown that antisense polynucleotides can inhibit in vitro activity (e.g., splicing).

Antisense polynucleotides can be DNA or RNA. They can be chemically modified so as to improve stability in the body. Properties of the polynucleotide can be engineered to impart stability (e.g., nuclease resistance), tighter binding or the desired $T_m$. For example, the polynucleotide can include modified nucleotide analogs, such as those already described. The polynucleotide can comprise mixtures of naturally occurring nucleotides and nucleotide analogues. Other techniques for rendering polynucleotides nuclease-resistant include those described in International patent publication No. 94/12633.

The general approach to constructing various polynucleotides useful in inhibitory polynucleotide therapy has been reviewed by A. R. Vander Krol et al. (1988), *Biotechniques* 6:958-976, and by C. A. Stein et al., (1988) *Cancer Res.* (1988) 48:2659-2668. See also *Oligodeoxynucleotides: Antisense Inhibitors of Gene Expression*, Cohen, J. S., editor, MacMillan Press, London, pages 79-196 (1989), and *Antisense RNA and DNA*, (1988), D. A. Melton, Ed., Cold Spring Harbor Laboratory, Cold Spring Harbor, N.Y.

In certain embodiments inhibitory polynucleotides comprise a derivatized substituent which is substantially non-interfering with respect to hybridization of the inhibitory polynucleotide to the target polynucleotide. Typically such inhibitory polynucleotides are derivatized, and additional chemical substituents are attached, either during or after polynucleotide synthesis, respectively, and are thus localized to a complementary sequence in the target polynucleotide where they produce an alteration or chemical modification to a local DNA sequence and/or to a protein component.

Preferred attached chemical substituents include: europium (III) texaphyrin, cross-linking agents, psoralen, metal chelates (e.g., iron/EDTA chelate for iron catalyzed cleavage), topoisomerases, endonucleases, exonucleases, ligases, phosphodiesterases, photodynamic porphyrins, chemotherapeutic drugs (e.g., adriamycin, doxirubicin), intercalating agents, base-modification agents, immunoglobulin chains, and oligonucleotides. Iron/EDTA chelates are particularly preferred chemical substituents where local cleavage of a polynucleotide sequence is desired (Hertzberg et al. (1982) *J. Am. Chem. Soc.* 104:313; Hertzberg and Dervan (1984) *Biochemistry* 23:3934; Taylor et al. (1984) *Tetrahedron* 40:457; P. B. Dervan (1986) *Science* 232:464).

Preferred attachment chemistries include: direct linkage, e.g., via an appended reactive amino group (Corey and Schultz (1988) *Science* 238:1401) and other direct linkage chemistries, although streptavidin/biotin and digoxigenin/anti-digoxigenin antibody linkage methods may also be used. Methods for linking chemical substituents are provided in U.S. Pat. Nos. 5,135,720, 5,093,245, and 5,055,556. Other linkage chemistries may be used at the discretion of the practitioner.

Polynucleotides which correspond to all or a substantial portion of a mammalian telomerase RNA component (i.e., "sense" polynucleotides) may also be derivatized and used to react with telomeric repeat sequences in the genome and produce adducts or other modification of the chemical environment at telomere regions of the chromosomes.

B. Antisense

This invention provides antisense polynucleotides capable of specifically hybridizing to a target sequence of the RNA component of telomerase, e.g., hTR. Antisense polynucleotides are useful in vitro or in vivo to inhibit the activity of telomerase.

The antisense polynucleotides of this invention comprise an antisense sequence of at least 7 nucleotides that specifically hybridize to a sequence from the RNA component of telomerase and, more particularly, mammalian telomerase and human telomerase. In one aspect of the invention, the RNA sequence to which the antisense sequence specifically hybridizes is within an accessible region of the telomerase RNA component. For example, the accessible region can be selected from the range of nucleotides 137-196, 290-319, or 350-380 of hTR. In one embodiment, the antisense polynucleotide does not hybridize to a sequence within the template region of telomerase.

The antisense sequence can be between about 10 and about 50 nucleotides or between 15 and about 35 nucleotides. In one embodiment, the sequence of the polynucleotide contains within it the antisense sequence. In this case, the antisense sequence is contained within a polynucleotide of longer sequence. In another embodiment, the sequence of the polynucleotide consists essentially of, or is, the antisense sequence. Thus, for example, the antisense polynucleotide can be a polynucleotide of less than about 50 nucleotides in a sequence that specifically hybridizes to the target sequence, e.g., an accessible region of the RNA component of telomerase.

Generally, to assure specific hybridization, the antisense sequence is substantially complementary to the target sequence in the RNA component of telomerase. In certain embodiments, the antisense sequence is exactly complementary to the target sequence. The antisense polynucleotides may include nucleotide substitutions, additions, deletions, or transpositions, so long as specific binding to the relevant target sequence corresponding to telomerase RNA component or its gene is retained as a functional property of the polynucleotide.

The antisense polynucleotide should be long enough to form a stable duplex but short enough, depending on the mode of delivery, to administer in vivo, if desired. The minimum length of a polynucleotide required for specific hybridization to a target sequence depends on several factors, such as G/C content, positioning of mismatched bases (if any), degree of uniqueness of the sequence as compared to the population of target polynucleotides, and chemical nature of the polynucleotide (e.g., methylphosphonate backbone, polyamide nucleic acid, phosphorothioate, etc.), among others. Antisense polynucleotides of the invention are polynucleotides of at least 7 nucleotides and can be between about 10 and 50 nucleotides or between about 15 and 30 nucleotides. In other embodiments, antisense polynucleotides are polynucleotides of less than about 100 nucleotides or less than about 200 nucleotides.

Antisense oligonucleotides directed against the sequence of the RNA component of telomerase are also described in U.S. application Ser. No. 08/272,102, filed Jul. 7, 1994; Ser. No. 08/472,802, filed Jun. 7, 1995; Ser. No. 08/521,634, filed Aug. 31, 1995; Ser. No. 08/630,019, filed Apr. 9, 1996; International Application PCT/US95/08530, filed Jul. 6, 1995; and U.S. Pat. No. 5,583,016.

Particularly useful antisense polynucleotides of the invention include those presented in Table 1 and FIG. 1, such as:

```
CGT TCC TCT TCC TGC GGC CTG      (SEQ ID NO:2)
AAA CGG TGA

CGT TCC TCT TCC TGC GGC CT       (SEQ ID NO:3)

CGT TCC TCT TCC                  (SEQ ID NO:4)

CTG ACA GAG CCC AAC TCT TCG      (SEQ ID NO:5)
CGG TGG CAG

CTG ACA GAG CCC AAC TCT TC       (SEQ ID NO:6)

CCA ACT CTT CGC GGT GGC AG       (SEQ ID NO:7)

GCT CTA GAA TGA ACG GTG GAA      (SEQ ID NO:8)
GGC GGC AGG

GCT CTA GAA TGA ACG GTG G        (SEQ ID NO:9)

GCT CTA GAA TGA ACG              (SEQ ID NO:10)

GCT CTA GAA TG                   (SEQ ID NO:11)

GCT CTA G                        (SEQ ID NO:12)

CAT TTT TTG TTT GCT CTA GA       (SEQ ID NO:13) and

CGG GCC AGC AGC TGA CA           (SEQ ID NO:14).
```

Accordingly, a sequence of the antisense polynucleotide can specifically hybridize to all or part of the telomerase RNA component sequence, such as antisense polynucleotides to the human telomerase RNA component gene or its transcribed RNA, including truncated forms which may be associated with telomerase ribonucleoprotein. Antisense polynucleotides directed against the RNA component in the telomerase ribonucleoprotein can be targeted against the template region.

Telomerase RNA component expression (transcription rate and/or RNA stability) is associated with activation and enzymatic activity of telomerase ribonucleoprotein. Therefore, antisense polynucleotides that prevent transcription of RNA corresponding to telomerase RNA component; the interaction of telomerase RNA component to the protein component of human telomerase and/or the interaction of telomerase RNA component to telomeric sequences inhibit telomerase activity. Inhibiting telomerase activity is useful to inhibit immortalization or neoplastic transformation of cells expressing telomerase activity in the absence of antisense polynucleotides.

For general methods relating to antisense polynucleotides, see *Antisense RNA and DNA*, (1988), D. A. Melton, Ed., Cold Spring Harbor Laboratory, Cold Spring Harbor, N.Y.). For a review of antisense therapy, see, e.g., Uhlmann et al., *Chem. Reviews*, 90:543-584 (1990).

The formation of a double-stranded polynucleotide resulting from hybridization of an antisense DNA molecule to the RNA component of telomerase renders the RNA component susceptible to RNase H cleavage. Accordingly, antisense polynucleotides directed against the RNA component of telomerase are particularly effective for inhibiting telomerase activity in cells or samples containing RNase H.

C. Ribozymes

Cleavage of the RNA component of telomerase can be induced by the use of ribozymes or catalytic RNA. In this approach, the ribozyme would contain either naturally occurring RNA (ribozymes) or synthetic nucleic acids with catalytic activity. Bratty et al., (1992) *Biochim. Biophys. Acta.*, 1216:345-59 (1993) and Denhardt, (1992) *Ann. N.Y. Acad. Sci.*, 660:70-76 describe methods for making ribozymes.

Unlike the antisense and other polynucleotides described above, which bind to an RNA, a DNA, or a telomerase protein component, a ribozyme not only binds but also specifically cleaves and thereby potentially inactivates a target RNA, such as the RNA component of telomerase. Such a ribozyme can comprise 5'- and 3'-terminal sequences complementary to the telomerase RNA. In one embodiment, the ribozyme is directed to an accessible region of the telomerase RNA component, e.g., not including the template region.

Depending on the site of cleavage, a ribozyme can render the telomerase enzyme inactive. See International application WO 93/23572. Upon review of the RNA sequence of the human telomerase RNA component those in the art will note that several useful ribozyme target sites are present and susceptible to cleavage by, for example, a hammerhead motif ribozyme. Optimum target sites for ribozyme-mediated inhibition of telomerase activity can be determined as described by Sullivan et al., PCT patent publication No. 94/02595 and Draper et al., PCT patent publication No. 93/23569. As described by Hu et al., PCT patent publication No. 94/03596, antisense and ribozyme functions can be combined in a single polynucleotide.

Such engineered ribozymes can be expressed in cells or can be transferred by a variety of means (e.g., liposomes, immunoliposomes, biolistics, direct uptake into cells, etc.). Other forms of ribozymes (group I intron ribozymes (Cech (1995) *Biotechnology* 13; 323); hammerhead ribozymes (Edgington (1992) *Biotechnology* 10: 256) can be engineered on the basis of the disclosed telomerase RNA component sequence information to catalyze cleavage of human telomerase RNA component and/or human telomere repeat sequences.

Moreover, ribozymes can comprise one or more modified nucleotides or modified linkages between nucleotides, as described above in conjunction with the description of antisense polynucleotides. In one aspect, a catalytic subunit of RNase P (human or *E. coli*) is modified (see, Altman (1995) *Biotechnology* 13: 327) to generate a guide sequence which corresponds to the portion of mammalian telomerase RNA component which base-pairs to the telomere repeat sequence; such RNase P variants can cleave telomere sequences. In one aspect, a catalytic subunit of RNase P (human or *E. coli*) is modified to generate a guide sequence which is complementary to a portion of telomerase RNA component such that the RNase P variant can cleave telomerase RNA component.

D. Other Inhibitory Polynucleotides

In addition to the antisense and ribozyme inhibitory polynucleotides, one can construct polynucleotides that will bind to duplex nucleic acid either in the folded RNA component or in the gene for the RNA component, forming a triple helix-containing or triplex nucleic acid to inhibit telomerase activity. Such polynucleotides of the invention are constructed using the base-pairing rules of triple helix formation and the nucleotide sequence of the RNA component (Cheng et al. (1988) *J. Biol. Chem.* 263: 15110; Ferrin and Camerini-Otero (1991) *Science* 354: 1494; Ramdas et al. (1989) *J. Biol. Chem.* 264: 17395; Strobel et al. (1991) *Science* 254: 1639; Hsieh et al. (1990) op.cit.; Rigas et al. (1986) *Proc. Natl. Acad. Sci. (U.S.A.)* 83: 9591. Such polynucleotides can block telomerase activity in a number of ways, including by preventing transcription of the telomerase gene or by binding to a duplex region of the RNA component of telomerase in a manner that prevents the RNA component either from forming a functional ribonucleoprotein telomerase or from serving as a template for telomeric DNA synthesis.

Typically, and depending on mode of action, the triplex-forming polynucleotides of the invention comprise a sequence large enough to form a stable triple helix but small enough, depending on the mode of delivery, to administer in vivo.

In another aspect, the invention provides inhibitory polynucleotides comprising a portion of the sequence of the RNA component of telomerase. In one embodiment the polynucleotide has a sequence sufficient to bind to a protein component of telomerase, but not sufficient to create a functional telomerase ribonucleoprotein. Such molecules are useful as decoys. Produced in sufficient quantities, they compete with functional RNA component for existing protein components, thereby decreasing the amount of functional telomerase, and telomerase activity, in a cell.

E. Methods of Making Inhibitory Polynucleotides

Inhibitory polynucleotides can be made chemically or recombinantly.

1. Chemical Synthesis

Small inhibitory polynucleotides for direct delivery can be made by chemical synthesis. Chemically synthesized polynucleotides can be DNA or RNA, or can include nucleotide analogs or backbones that are not limited to phosphodiester linkages.

2. Recombinant Production

For delivery into cells or for gene therapy methods, recombinant production of inhibitory polynucleotides through the use of expression vectors is particularly useful. Accordingly, this invention also provides expression vectors, e.g., recombinant polynucleotides comprising expression control sequences operatively linked to the nucleotide sequence encoding the inhibitory polynucleotide. Expression vectors can be adapted for function in prokaryotes or eukaryotes (e.g., bacterial, mammalian, yeast, *Aspergillus*, and insect cells) by inclusion of appropriate promoters, replication sequences, markers, etc. for transcription and translation of mRNA. The construction of expression vectors and the expression of genes in transfected cells involves the use of molecular cloning techniques also well known in the art. Sambrook et al., *Molecular Cloning—A Laboratory Manual*, Cold Spring Harbor Laboratory, Cold Spring Harbor, N.Y., (1989), *Current Protocols in Molecular Biology*, F. M. Ausubel et al., eds., (Current Protocols, a joint venture between Greene Publishing Associates, Inc. and John Wiley & Sons, Inc.) and Berger and Kimmel, *Methods in Enzymology, Volume* 152, *Guide to Molecular Cloning Techniques* (1987), Academic Press, Inc., San Diego, Calif. Useful promoters for such purposes include a metallothionein promoter, a constitutive adenovirus major late promoter, a dexamethasone-inducible MMTV promoter, a SV40 promoter, a MRP polIII promoter, a constitutive MPSV promoter, a tetracycline-inducible CMV promoter (such as the human immediate-early CMV promoter), and a constitutive CMV promoter. A plasmid useful for gene therapy can comprise other functional elements, such as selectable markers, identification regions, and other genes. Recombinant DNA expression plasmids can also be used to prepare the polynucleotides of the invention for delivery by means other than by gene therapy, although it may be more economical to make short oligonucleotides by in vitro chemical synthesis.

Methods of transfecting genes into mammalian cells and obtaining their expression for in vitro use or for gene therapy, are well known to the art. See, e.g., *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y., (1990). Cells can be transfected with plasmid vectors, for example, by electroporation. Cells can be transfected by polynucleotides by calcium phosphate precipitation DNA liposome complexes, by particle-mediated gene transfer (biolistics) or with liposomes.

Expression vectors useful in this invention depend on their intended use. Such expression vectors must, of course, contain expression and replication signals compatible with the host cell. Expression vectors useful for expressing the inhibitory polynucleotide of this invention include viral vectors such as retroviruses, adenoviruses and adeno-associated viruses, plasmid vectors, cosmids, liposomes and the like. Viral and plasmid vectors are preferred for transfecting mammalian cells. The expression vector pcDNA1 (Invitrogen, San Diego, Calif.), in which the expression control sequence comprises the CMV promoter, provides good rates of transection and expression. Adeno-associated viral vectors are useful in the gene therapy methods of this invention.

IV. Methods of Inhibiting Telomerase Activity

This invention provides methods of inhibiting telomerase activity either in vitro or in vivo by contacting telomerase with an inhibitory polynucleotide of the invention. Such methods are useful both in samples containing telomerase as well as in living cells, either cultured or in vivo in methods of treatment. In cells, inhibition of telomerase activity renders an immortal cell mortal. Telomerase inhibition therapy is an effective treatment against cancers involving the uncontrolled growth of immortal cells. Delivery of inhibitory polynucleotides against the RNA component of telomerase prevent telomerase action and ultimately leads to cell senescence and cell death of treated cells.

In one method of the invention, inhibiting telomerase involves contacting telomerase with an inhibitory polynucleotide directed against the template region of the RNA component of telomerase, and with an inhibitory polynucleotide directed against an accessible region of the RNA component of telomerase, but which does not specifically hybridize to the template region.

A. In Vitro

The inhibitory polynucleotides of this invention are useful for inhibiting telomerase activity in vitro. Such methods are useful as controls in screening assays to identify other molecular inhibitors of telomerase activity. The methods involve contacting the telomerase with an inhibitory polynucleotide of this invention, for example, by adding it to a sample solution.

B. In Cells

Inhibitory polynucleotides against telomerase are useful for inhibiting telomerase activity in both cultured cells and in cells in vivo. Inhibiting telomerase activity in cultured cells is useful for mortalizing those cells. For example, immortal cell lines can be made mortal. Immortalized cells from a subject can be mortalized by the introduction of an inhibitory polynucleotide and then re-introduced into a subject in a prophylactic or therapeutic treatment of a subject. The inhibition of telomerase activity in cells in vivo is useful in prophylactic and therapeutic methods of treating cancer and other disorders involving over-expression of telomerase.

This invention contemplates a variety of means for delivering an inhibitory polynucleotide to a subject including, for example, direct uptake of the molecule by a cell from solution, facilitated uptake through lipofection (e.g., liposomes or immunoliposomes), particle-mediated transfection, and intracellular expression from an expression cassette having an expression control sequence operably linked to a nucleotide sequence that encodes the inhibitory nucleic acid.

One can provide a cell with an inhibitory polynucleotide by contacting the cell with a soluable inhibitory nucleic acid, for example, in the culture medium in vitro or in the circulatory system, interstitial fluid or tissue mass in vivo. Soluble inhibitory nucleic acids present in the external milieu have been shown to gain access to the cytoplasm. Methods useful for delivery of polynucleotides for therapeutic purposes are described in Inouye et al., U.S. Pat. No. 5,272,065.

V. Prophylactic and Therapeutic Methods

This invention provides methods of treating conditions in mammals involving undesirable expression of telomerase activity. The methods involve administering to the subject an amount of an inhibitory polynucleotide of this invention effective to inhibit telomerase activity (a pharmacologically effective amount). Cells that express telomerase activity and that can be targets of telomerase inhibition therapy include telomerase expressing cancer cells, germ-line cells and telomerase expressing hematopoietic cells. Inhibiting telomerase activity is also useful in treating veterinary proliferative diseases. Because telomerase is active only in tumor, germline, and certain stem cells of the hematopoietic system, other normal cells are not affected by telomerase inhibition therapy. Steps can also be taken to avoid contact of the telomerase inhibitor with germline or stem cells, if desired, although this may not be essential.

A. Cancer

The mechanisms that control the cell cycle in normal cells go awry in cancer cells. Consequently, these cells continue to divide when normal cells would not divide. Most cancer cells exhibit telomerase activity. As a consequence, these cells maintain the ability to divide after the number of cell divisions in which normal somatic cells usually reach senescence. Thus, inhibition of telomerase activity in telomerase-expressing cancer cells results in eventual cell crisis and senescence. Inhibitory polynucleotides that inhibit telomerase activity are useful in treating or preventing cancer. Types of cancer that can be treated include, for example, adenocarcinoma of the breast, prostate, and colon; all forms of bronchogenic carcinoma of the lung; leukemias such as mixed cell, T-cell chronic, lymphocytic acute, lymphocytic chronic, and myeloid; Hodgkin's disease; melanoma; hepatoma; neuroblastoma; and papilloma.

B. Germ-Line Cells

Germ-line cells, i.e., oocytes and sperm, express telomerase activity. Therefore, inhibition of telomerase activity in germ-line cells is useful for methods of contraception or sterilization.

C. Hematopoietic Stem Cells

Hematopoietic stem cells express telomerase. Therefore, inhibition of telomerase in such cells is useful for immunosuppression and for selectively down-regulating specific branches of the immune system, e.g., a specific subset of T cells. Such methods are useful in anti-inflammatory therapies. Inhibiting telomerase in certain branches of cells using inhibitory polynucleotides is attractive because after therapeutic effect, the treatment can be halted and stem cells will repopulate the system with healthy cells.

D. Infection by Eukaryotic Organisms

Eukaryotic organisms that express telomerase, e.g., yeast, parasites and fungi, can infect the body. Such infections can be treated by inhibiting telomerase in these organisms, thereby halting growth of the organism.

E. Administration

Inhibitory polynucleotides and vectors for expressing them can be delivered conveniently in the form of a pharmaceutical composition comprising a pharmaceutically acceptable carrier and a pharmacologically effective amount of the agent. The pharmaceutical composition can be administered by any means known in the art for delivery of such molecules. However, systemic administration by injection is preferred. This includes intramuscular, intravenous, intraperitoneal, and subcutaneous injection. The pharmaceutical compositions can be administered in a variety of unit dosage forms depending upon the method of administration. For example, unit dosage forms for parenteral administration include unit doses of injectable solutions.

The form, amounts and timing of administration generally are a matter for determination by the practitioner. In one embodiment, the pharmaceutical composition is delivered as a unit dosage form. Dosages include about of $10^7$ to $10^{13}$ particles of viral vector per ml of carrier. The volume administered can be selected by the practitioner. According to one embodiment of this invention, approximately $10^{10}$ vectors suspended in about 1 ml of sterile PBS constitute a therapeutically effective amount.

VI. Purification of Telomerase

Antisense polynucleotides directed against accessible regions of the RNA component of telomerase are useful as affinity reagents for purifying telomerase. Such methods involve immobilizing the antisense polynucleotide on a solid support, contacting the telomerase with the antisense polynucleotide, removing molecules not bound to the support, and isolating telomerase from the support. Methods for purifying telomerase using affinity reagents are described in U.S. application Ser. No. 08/510,736, filed Aug. 4, 1995.

The following example is given to illustrate but not limit the invention.

EXAMPLE

A set of 17 contiguous antisense DNA oligonucleotides (30 mers) were tested for their ability to direct RNase H cleavage of hTR in the context of the native telomerase enzyme. Three antisense DNA 30 mers (denoted "14", "16", and "21") directed efficient cleavage of hTR, indicating that the corresponding regions of hTR were accessible to DNA probes in the intact ribonucleoprotein particle (RNP). Antisense oligonucleotides "14", "16", and "21" (see Table I) were tested as potential inhibitors of human telomerase ("hTase"). These regions corresponded to nucleotides 350-380, 290-319 and 137-196 of hTR.

Preincubation of partially purified nuclear or cytoplasmic extract with antisense oligonucleotide "21" (directed against nucleotides 137 to 166 of hTR) resulted in potent inhibition of hTase, as indicated by the standard primer elongation assay. Antisense oligonucleotides "14" and "16" and a "sense" oligonucleotide did not significantly affect hTase activity. A 20 mer antisense oligonucleotide comprised of 2'-o-methyl RNA directed against nucleotides 147 to 166 of hTR also inhibited hTase. The concentration of antisense oligonucleotide that yielded 50% hTase inhibition (IC50) was estimated from an activity versus antisense oligo concentration profile. The ICSOs for the 20 mer and 30 mer antisense oligonucleotides were in the range of 1 to 10 nanomolar (antisense oligo:hTase at IC50=3:1). Control antisense oligonucleotide yielded no inhibition of hTase at oligo concentrations of 600 to 2000 nanomolar. A northern analysis showed that hTR remained intact throughout the inhibition protocol, suggesting the antisense inhibition of hTase was independent of RNase H activity.

The accessible regions were "fine mapped" by using shorter antisense oligonucleotides to direct RNase H cleavage of hTR. For the "14" region, a 20 mer (14ab) and a 12 mer (14d) directed RNase H cleavage. For the "16" region, two 20 mers (16ab, 16bc) directed RNase H cleavage. For the "21" regions, an antisense oligo as small as 7 nucleotides directed RNase H cleavage within the 147-166 region of hTR. Hence, these "short" antisense oligonucleotides might also inhibit hTase. A map summarizing antisense sequences able to direct RNase H cleavage of hTR in the native ribonucleoprotein is shown in FIG. 1.

TABLE 1

| Oligo # | Sequence | RnaseH Digestion? | Capture? (2 'Ome) | Activity on beads | NB ref GLN-21 |
|---|---|---|---|---|---|
| 14 | 5' CGT TCC TCT TCC TGC GGC CTG AAA CGG TGA 3' (SEQ ID NO. 2) | yes | | | 73 |
| 14ab | 5' CGT TCC TCT TCC TGC GGC CT 3' (SEQ ID NO. 3) | yes | yes | yes | 92 |
| 14bc | 5' CCT GCG GCC TGA AAC GGT GA 3' (SEQ ID NO. 15) | no | NA | NA | 92 |

TABLE 1-continued

| Oligo # | Sequence | RnaseH Digestion? | Capture? (2'Ome) | Activity on beads | NB ref GLN-21 |
|---|---|---|---|---|---|
| 14d | 5' CGT TCC TCT TCC 3' (SEQ ID NO. 4) | yes | yes | yes | 106 |
| 16 | 5' CTG ACA GAG CCC AAC TCT TCG CGG TGG CAG 3' (SEQ ID NO. 5) | yes | | | 73 |
| 16ab | 5' CTG ACA GAG CCC AAC TCT TC 3' (SEQ ID NO. 6) | yes | yes | no | 92 |
| 16bc | 5' CCA ACT CTT CGC GGT GGC AG 3' (SEQ ID NO. 7) | yes | yes | NT | 92 |
| 21 | 5' GCT CTA GAA TGA ACG GTG GAA GGC GGC AGG 3' (SEQ ID NO. 8) | yes | | | 73, 13 |
| 21ab | 5' GCT CTA GAA TGA ACG GTG G 3' (SEQ ID NO. 9) | yes | yes | * | 177 |
| 21ab3 | 5' GCT CTA GAA TGA ACG 3' (SEQ ID NO. 10) | yes | NT | * | 177 |
| 21ab2 | 5' GCT CTA GAA TG 3' (SEQ ID NO. 11) | yes | yes | NT | 177 |
| 21ab1 | 5' GCT CTA G 3' (SEQ ID NO. 12) | yes | yes | yes | 177 |
| 20/21 | 5' CAT TTT TTG TTT GCT CTA GA 3' (SEQ ID NO. 13) | yes | NT | NT | 177 |

NA = not applicable
NT = not tested
*known to inhibit telomerase

On the bases of the antisense data, biotinylated 2'OMe antisense RNA analogs were designed for affinity purification of telomerase. The goal of the antisense affinity approach was to design ligands that afforded good purification and yield, while keeping the enzyme intact (i.e., active). Several 2'OMe ligands met our criteria (Table 1, FIG. 1). The biotinylated 2'O Me analogs of 14ab and 14d, as well as the 21ab1 analog, "captured" active telomerase on streptavidin beads. These analogs were further refined via the synthesis of second generation antisense affinity ligands, which were designed to allow release of active telomerase (reversible ligands). Currently, our affinity scheme consists of two reversible antisense ligands, which are employed in series, and target two different regions of hTR. The first ligand is a disulfide version of 14ab which allows release of telomerase via dithiothreitol treatment. The second ligand contains the 21ab1 antisense sequence and plus a tail of "nonsense" sequence. hTR is released from the antisense ligand by a displacement DNA oligonucleotide, which is complementary to the entire length of the 21ab1 antisense affinity ligand.

Oligodecoration was used to further identify accessible regions of the telomerase ribonucleoprotein. Radioactively labeled 2'O-methyl antisense polynucleotides were prepared and exposed to the telomerase ribonucleoprotein. The sample was incubated to allow the polynucleotide to bind to telomerase. Then the sample was run on a native gel. Polynucleotides that had bound to telomerase exhibited altered mobility on the gel. In particular, polynucleotides RP2 and RP3 (FIG. 1) were found to bind to the telomerase ribonucleoprotein. RP2 has the sequence CGG GCC AGC AGC TGA CA (SEQ ID NO:14). This demonstrated that nucleotides 167-196 also are accessible to antisense polynucleotides. RP2 demonstrated an ability to capture telomerase on an affinity matrix and is useful for purifying telomerase.

The present invention provides novel methods for inhibiting telomerase activity. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A composition consisting of a polynucleotide and a pharmaceutically acceptable carrier,
   wherein the polynucleotide
   (a) has a sequence of at least 10 nucleotides that specifically hybridizes to a first nucleotide sequence within an accessible region of the RNA component of a human telomerase (hTR), wherein the accessible region is selected from the group consisting of nucleotides 290-319 and nucleotides 350-380 of hTR (SEQ ID NO:16),
   (b) does not hybridize to a second nucleotide sequence within the template region of the hTR, said template region being nucleotides 46-55 of SEQ ID NO:16, and
   (c) is effective to inhibit the synthesis of telomeric DNA by telomerase.

2. The composition of claim 1, wherein said polynucleotide has a sequence of about 15 to about 35 nucleotides that specifically hybridizes to the first nucleic acid sequence.

3. The composition of claim 1, wherein said polynucleotide comprises a nucleotide analog or a non-naturally occurring nucleotide linkage selected from the group consisting of phosphorothioates, phosphoramidates, methyl phosphonates, chiral methyl phosphonates, 2'-O-methyl ribonucleotides and peptide nucleic acids.

4. A polynucleotide consisting of a sequence selected from the group consisting of:

| | |
|---|---|
| CGT TCC TCT TCC TGC GGC CTG AAA CGG TGA | (SEQ ID NO:2) |
| CGT TCC TCT TCC TGC GGC CT | (SEQ ID NO:3) |
| CGT TCC TCT TCC | (SEQ ID NO:4) |
| CTG ACA GAG CCC AAC TCT TCG CGG TGG CAG | (SEQ ID NO:5) |
| CTG ACA GAG CCC AAC TCT TC | (SEQ ID NO:6) |
| CCA ACT CTT CGC GGT GGC AG | (SEQ ID NO:7) |
| GCT CTA GAA TGA ACG GTG G | (SEQ ID NO:9) |
| GCT CTA GAA TGA ACG | (SEQ ID NO:10) |
| GCT CTA GAA TG | (SEQ ID NO:11) |
| GCT CTA G | (SEQ ID NO:12) |
| CAT TTT TTG TTT GCT CTA GA | (SEQ ID NO:13) and |
| CGG GCC AGC AGC TGA CA | (SEQ ID NO:14). |

5. A composition comprising the polynucleotide as recited in claim 4 in a pharmaceutically acceptable carrier.

6. The composition of claim 1, wherein said polynucleotide comprises a sequence of at least 10 nucleotides that specifically hybridizes to the first nucleotide sequence within an accessible region of the RNA component of a human telomerase (hTR), said accessible region being nucleotides 290-319 of SEQ ID NO:16.

7. The composition of claim 1, wherein said polynucleotide comprises a sequence of at least 10 nucleotides that specifically hybridizes to the first nucleotide sequence within an accessible region of the RNA component of a human telomerase (hTR), said accessible region being nucleotides 350-380 of SEQ ID NO:16.

8. The composition of claim 1, wherein said polynucleotide has a sequence of about 10 to about 50 nucleotides that specifically hybridizes to the first nucleic acid sequence.

9. The composition of claim 5, wherein said polynucleotide comprises a nucleotide analog or a non-naturally occurring nucleotide linkage selected from the group consisting of phosphorothioates, phosphoramidates, methyl phosphonates, chiral methyl phosphonates, 2'-O-methyl ribonucleotides and peptide nucleic acids.

* * * * *

SEQUENCE LISTING

```
<160> NUMBER OF SEQ ID NOS: 16

<210> SEQ ID NO 1
<211> LENGTH: 981
<212> TYPE: DNA
<213> ORGANISM: Homo sapiens

<400> SEQUENCE: 1
ctgcagagga tagaaaaaag gccctctgat acctcaagtt agtttcacct ttaaagaagg        60
tcggaagtaa agacgcaaag cctttccggg acgtgcggaa gggcaacgtc cttcctcatg       120
gccggaaatg gaactttaat ttcccgttcc ccccaaccag cccgcccgag agagtgactc       180
tcacgagagc cgcgagagtc agcttggcca atccgtgcgg tcggcggccg ctcccttttat      240 aagccgactc gcccggcagc gcaccgggtt gcggagggtg ggcctgggag gggtggtggc       300
cattttttgt ctaaccctaa ctgagaaggg cgtaggcgcc gtgcttttgc tccccgcgcg       360
```

-continued

```
ctgttttcct cgctgactt  cagcgggcgg aaaagcctcg gcctgccgcc ttccaccgtt    420
cattctagag caaacaaaaa atgtcagctg ctggcccgtt cgcccctccc ggggacctgc    480
ggcgggtcgc ctgcccagcc cccgaacccc gcctggaggc cgcggtcggc ccggggcttc    540
tccggaggca cccactgcca ccgcgaagag ttgggctctg tcagccgcgg gtctctcggg    600
ggcgagggcg aggttcaggc ctttcaggcc gcaggaagag gaacggagcg agtccccgcg    660
cgcggcgcga ttccctgagc tgtgggacgt gcacccagga ctcggctcac acatgcagtt    720
cgctttcctg ttggtggggg gaacgccgat cgtgcgcatc cgtcacccct cgccggcagt    780
gggggcttgt gaaccccaa  acctgactga ctgggccagt gtgctgcaaa ttggcaggag    840
acgtgaaggc acctccaaag tcggccaaaa tgaatgggca gtgagccggg gttgcctgga    900
gccgttcctg cgtgggttct cccgtcttcc gcttttgtt  gccttttatg gttgtattac    960
aacttagttc ctgctctgca g                                              981
```

<210> SEQ ID NO 2
<211> LENGTH: 30
<212> TYPE: DNA
<213> ORGANISM: Homo sapiens

<400> SEQUENCE: 2

```
cgttcctctt cctgcggcct gaaacggtga                                      30
```

<210> SEQ ID NO 3
<211> LENGTH: 20
<212> TYPE: DNA
<213> ORGANISM: Homo sapiens

<400> SEQUENCE: 3

```
cgttcctctt cctgcggcct                                                 20
```

<210> SEQ ID NO 4
<211> LENGTH: 12
<212> TYPE: DNA
<213> ORGANISM: Homo sapiens

<400> SEQUENCE: 4

```
cgttcctctt cc                                                         12
```

<210> SEQ ID NO 5
<211> LENGTH: 30
<212> TYPE: DNA
<213> ORGANISM: Homo sapiens

<400> SEQUENCE: 5

```
ctgacagagc ccaactcttc gcggtggcag                                      30
```

<210> SEQ ID NO 6
<211> LENGTH: 20
<212> TYPE: DNA
<213> ORGANISM: Homo sapiens

<400> SEQUENCE: 6

```
ctgacagagc ccaactcttc                                                 20
```

<210> SEQ ID NO 7
<211> LENGTH: 20
<212> TYPE: DNA
<213> ORGANISM: Homo sapiens

<400> SEQUENCE: 7

-continued ccaactcttc gcggtggcag                                              20

<210> SEQ ID NO 8
<211> LENGTH: 30
<212> TYPE: DNA
<213> ORGANISM: Homo sapiens

<400> SEQUENCE: 8
gctctagaat gaacggtgga aggcggcagg                                   30

<210> SEQ ID NO 9
<211> LENGTH: 19
<212> TYPE: DNA
<213> ORGANISM: Homo sapiens

<400> SEQUENCE: 9
gctctagaat gaacggtgg                                               19

<210> SEQ ID NO 10
<211> LENGTH: 15
<212> TYPE: DNA
<213> ORGANISM: Homo sapiens

<400> SEQUENCE: 10
gctctagaat gaacg                                                   15

<210> SEQ ID NO 11
<211> LENGTH: 11
<212> TYPE: DNA
<213> ORGANISM: Homo sapiens

<400> SEQUENCE: 11
gctctagaat g                                                       11

<210> SEQ ID NO 12
<211> LENGTH: 7
<212> TYPE: DNA
<213> ORGANISM: Homo sapiens

<400> SEQUENCE: 12 gctctag                                                             7

<210> SEQ ID NO 13
<211> LENGTH: 20
<212> TYPE: DNA
<213> ORGANISM: Homo sapiens

<400> SEQUENCE: 13 catttttgt ttgctctaga                                               20

<210> SEQ ID NO 14
<211> LENGTH: 17
<212> TYPE: DNA
<213> ORGANISM: Homo sapiens

<400> SEQUENCE: 14
cgggccagca gctgaca                                                 17

<210> SEQ ID NO 15
<211> LENGTH: 20
<212> TYPE: DNA
<213> ORGANISM: Homo sapiens

```
<400> SEQUENCE: 15
cctgcggcct gaaacggtga                                                    20

<210> SEQ ID NO 16
<211> LENGTH: 451
<212> TYPE: DNA
<213> ORGANISM: Homo sapiens

<400> SEQUENCE: 16
gggttgcgga gggtgggcct gggaggggtg gtggccattt tttgtctaac cctaactgag        60
aagggcgtag gcgccgtgct tttgctcccc gcgcgctgtt tttctcgctg actttcagcg       120
ggcggaaaag cctcggcctg ccgccttcca ccgttcattc tagagcaaac aaaaaatgtc       180
agctgctggc ccgttcgccc ctcccgggga cctgcggcgg gtcgcctgcc cagccccga       240 accccgcctg gaggccgcgg tcggcccggg gcttctccgg aggcacccac tgccaccgcg       300
aagagttggg ctctgtcagc cgcgggtctc tcggggcgga gggcgaggtt caggcctttc       360
aggccgcagg aagaggaacg gagcgagtcc ccgcgcgcgg cgcgattccc tgagctgtgg       420
gacgtgcacc caggactcgg ctcacacatg c                                      451
```